(12) United States Patent
Yasuda et al.

(10) Patent No.: US 6,703,132 B1
(45) Date of Patent: Mar. 9, 2004

(54) MAGNETORESISTANCE SENSOR ELEMENT AND METHOD OF FABRICATING THE MAGNETORESISTANCE ELEMENT

(75) Inventors: Naoki Yasuda, Tokyo (JP); Tatsuya Fukami, Tokyo (JP); Motohisa Taguchi, Tokyo (JP); Yuji Kawano, Tokyo (JP)

(73) Assignee: Mitsubishi Denki Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/890,103

(22) PCT Filed: Dec. 22, 1999

(86) PCT No.: PCT/JP99/07230

§ 371 (c)(1),
(2), (4) Date: Sep. 25, 2001

(87) PCT Pub. No.: WO01/46708

PCT Pub. Date: Jun. 28, 2001

(51) Int. Cl.⁷ .................................................. B32B 9/00
(52) U.S. Cl. ...................... 428/447; 428/450; 427/515; 324/244
(58) Field of Search ................... 428/447, 450; 427/515; 324/244

(56) References Cited

U.S. PATENT DOCUMENTS

| | | | |
|---|---|---|---|
| 4,473,813 A | 9/1984 | Kinjo et al. | |
| 4,732,042 A | 3/1988 | Adams | |
| 5,532,294 A | 7/1996 | Ikeno et al. | |
| 5,888,846 A | * 3/1999 | Miyata et al. | 438/105 |
| 6,154,028 A | * 11/2000 | Bushida et al. | 324/253 |

FOREIGN PATENT DOCUMENTS

| | | | |
|---|---|---|---|
| EP | 0 676 450 A2 | 2/1995 | |
| GB | 2322452 A | 8/1998 | |
| JP | 60-62278 A | 4/1985 | |
| JP | 60-62278 A2 * | 4/1985 | .......... H04N/5/335 |
| JP | 6-180038 A | 4/1986 | |
| JP | 62-163959 | 7/1987 | |
| JP | 62-178359 A | 8/1987 | |
| JP | 2-222537 | 9/1990 | |
| JP | 3-207719 | 9/1991 | |
| JP | 4-184160 | 7/1992 | |
| JP | 4-326032 | 11/1992 | |
| JP | 5-121793 | 5/1993 | |
| JP | 05-335613 | * 12/1993 | .......... H01L/31/08 |
| JP | 64-13616 A | 1/1998 | |
| JP | 64-54843 A | 2/1998 | |
| JP | 10-319597 | 12/1998 | |
| WO | JP99/07230 A1 | 12/1999 | |
| WO | WO 01/88482 | 11/2001 | |

* cited by examiner

*Primary Examiner*—James J. Seidleck
*Assistant Examiner*—Melanie Bissett
(74) *Attorney, Agent, or Firm*—Leydig, Voit & Mayer, Ltd.

(57) ABSTRACT

The invention provides a sensor element having a sensor substrate and a flat sensor portion supported by the sensor substrate in which the surface of the flat sensing portion is covered with a silicone resin film. The silicone resin film is excellent in step coverage of the flat sensing portion, having low stress applied to the sensing portion, can be formed at low temperature and can prevent the sensing portion from being effected with adverse influence even in the fabrication steps.

10 Claims, 5 Drawing Sheets

MAGNETORESISTANCE SENSOR ELEMENT
AND METHOD OF FABRICATING THE
MAGNETORESISTANCE ELEMENT

TECHNICAL FIELD

The present invention relates to a sensor element, particularly to a sensor such as a magiletoresistance sensor, an air flow sensor, an acceleration sensor, a pressure sensor, a yaw rate sensor, or an image sensor having a constant area sensor face.

BACKGROUND ART

Conventionally, an acceleration sensor, a yaw rate sensor, a pressure sensor, an air flow sensor, and a magnetoresistance sensor are used as sensor elements for controlling running of a vehicle. Among them, each of the acceleration sensor, the yaw rate sensor, and the pressure sensor includes a flat pivotally moving electrode (sensing portion) responding to impact or acceleration, and detecting a change in electric capacitance between the electrode and an opposed electrode fixedly arranged proximate the moving electrode. Further, various metal materials are used for the planar electrode constituting the sensing portion, for example, as described in Japanese Patent Laid-Open No. Hei. 5-183145. Japanese Patent Laid-Open No. Hei. 5-283712, or Japanese Patent Laid-Open No. Hei. 6-194382, a surface thereof is covered and protected by a silicon nitride film or a silicon oxide film, and these inorganic thin films are formed by sputtering, CVD, or another vapor deposition process.

However, the planar electrode is provided with a three-dimensional structure projected from a supporter for supporting the electrode in a plane direction (thickness is normally about 10 through 500 $\mu$m) and accordingly, coverage performance of an inorganic thin film by the vapor deposition process or the CVD process is poor, particularly, it is difficult to form the inorganic thin film at side faces of the planar electrode and there is a concern that protection performance is deteriorated.

Further, although an air flow sensor for detecting a flow rate of gasoline is constituted to detect a flow rate of a gas including gasoline by detecting a temperature variation of a sensing portion produced by bringing the sensing portion in a planar shape embedded with a resistance wiring into contact with a flow path of the gas including gasoline by a change in resistance of the resistance wiring, since the sensor is of a three-dimensional structure having a large stepped difference between the sensing portion and a supporter, with regard to protection of the sensing portion, a problem similar to the above-described is posed.

Therefore, it is conceivable to thicken the inorganic thickness to sufficiently protect side faces of the planar electrode by the inorganic thin film, however, high stress is caused at the sensing portion and crack is caused in the film per se. Thereby, there poses a problem that the sensor characteristic is deteriorated or a position shift is caused in the resistance wiring constituting the sensor portion or a wiring on a contiguous control circuit. Particularly, in the case of a sensor in which the wiring of the resistance wiring is used for the sensing portion, as the wiring, there is used a special material which is not used in a normal semiconductor element and therefore, depending on the constituting material, adherence with a substrate material is significantly weak, for example, when the sensor element is sealed by a resin, there poses a problem that such a wiring is liable to cause the positional shift by thermal or mechanical strain.

It is conceivable to use polyimide resin or photosensitive polyimide resin on sale as the protective film of the sensing portion, however, in view of stress characteristic, heat resistance, degasing performance and compatibility with fabrication process (processing temperature or the like), there is frequently a case in which adverse influence is effected on the characteristic of the sensing portion. That is, formation of a film of polyimide resin is carried out by chemical reaction in which polyimide is formed from amic acid monomer by chemical reaction and accordingly, residual stress is high and contamination is caused by gas components produced by the reaction. Further, a polyimide resin protective film is inferior in water proof performance and environment of using the sensor element is restricted.

SUMMARY OF THE INVENTION

Meanwhile, different from the above-described sensor having the three-dimensional structure, a magnetoresistance sensor is not basically provided with a significant stepped difference, provided with a sensing portion in a planar shape comprising slender wires of magnetic metal, constituted to be capable of detecting a change in magnitude or direction of a magnetic field by utilizing a magnetoresistance effect of a magnetic metal and although it is conceivable to protect the sensing portion by a polyimide resin film, however, it is necessary to carry out a curing processing at high temperature, the curing temperature is higher than heat resistance limit temperature of the main body of the sensor and there poses a problem that sufficient curing processing cannot be carried out.

The invention has been carried out under such a situation and it is an object thereof to provide a sensor element in which particularly, a sensing portion in a planar shape is coated with a protective film excellent in step coverage, having low stress applied to the sensing portion, capable of being formed at low temperature and having no concern of effecting adverse influence to the sensing portion even in a fabrication process.

DISCLOSURE OF THE INVENTION

According to the invention, there is provided a sensor element having a sensor substrate and a flat sensing portion supported by the sensor substrate, wherein the surface of the flat sensing portion is covered with a silicone resin film.

The silicone resin film used in the invention is provided with heat resistance against temperature in a process of fabricating the sensor element or used temperature, excellent in coverage performance, excellent in coverage performance of the flat sensing portion having the three-dimensional structure, provided with low stress performance, can be thickened and provided with high environment resistance. Further, according to the silicone resin film, different from polyimide resin used as a protective film in a semiconductor device, an amount of generating gas in curing the film is extremely small, and contamination is not caused not only at the sensing portion but also at a contiguous control circuit portion. Further, the silicone resin film exceeds polyimide resin in heat resistance, adhering performance and low stress performance. Further, the silicone resin film is more excellent than polyimide resin or a material of an inorganic film formed by a conventional CVD process or sputtering process in view of coverage performance.

The silicone resin film can be formed by coating a solution of the silicone polymer and heating and curing thereof. According to such forming method, by rotationally coating and heating thereof, the sensing portion can be covered and protected simply and effectively and adverse influence effected to the sensing portion as in the polyimide species protective film is resolved. Further, there is not used an expensive film forming apparatus as in an inorganic species protective film, which is advantageous in view of fabrication cost. Therefore, according to the invention, there is provided a method of fabricating a sensor constituted by covering the sensing portion by the silicone resin film by coating the solution of the silicone polymer to the flat sensing portion supported by the sensor substrate and heating and curing thereof.

BRIEF DESCRIPTION OF THE DRAWINGS

FIGS. 3A and 3B are views for explaining a structure of an air flow sensor of Embodiment 1 according to the invention in which FIG. 3A is a plane view and FIG. 3B is a sectional-25 view taken along a line IIIB—IIIB of FIG. 3A.

FIGS. 4A and 4B arc views for explaining a structure of an acceleration sensor of Embodiment 3 according to the invention in which FIG. 4A is a plane view and FIG. 4B is a sectional view taken along a line IVB—IVB of FIG. 4A.

BEST MODE FOR CARRYING OUT THE INVENTION

Figure 1A:
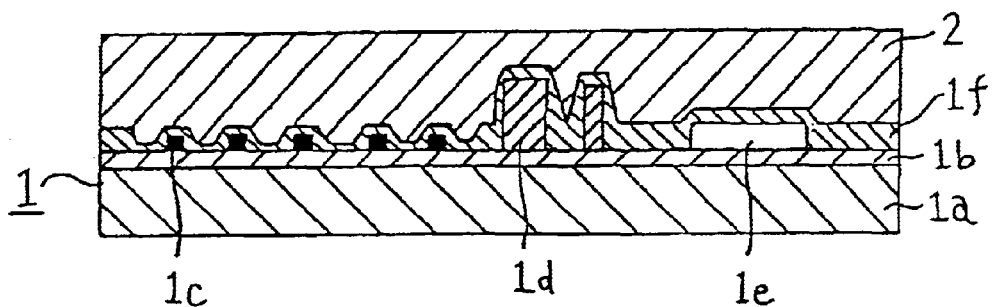
FIGS. 1A–1G are sectional views for explaining an example of a structure of a magnetoresistance sensor according to the invention and a method of fabricating thereof.
Figure 1B:
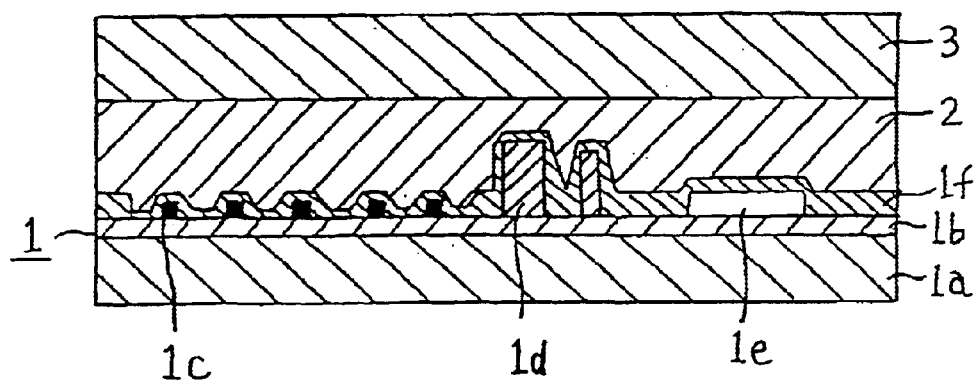

According to a sensor element of the invention, a surface or a total surface of a sensing portion in each of various sensors of an acceleration sensor, a yaw rate sensor, a pressure sensor, a magnetoresistance sensor, an image sensor and the like, is covered and protected by a silicone resin film. Further, although the sensing portion in the respective sensor element is normally constituted by a plane, there may be provided more or less irregularities and the sensing portion may be formed substantially in a plane shape. Further, there may be constructed a constitution in which a silicone resin film covers not only the sensing portion but also a contiguous substrate or a peripheral circuit.

The silicone resin film comprises a cured film of silicone polymer, as the silicone polymer, it is suitable to use silicone polymer represented by the general formula (1) shown below or silicone polymer represented by the general formula (2) shown below and these may be mixtures respectively. Particularly, the silicone polymer of the general formula (2) having a ladder structure is preferable since heat resistance thereof after curing is excellent, stress applied to a substrate material by the polymer per se is low, further, a buffer action against stress from outside is excellent.

General Formula (1);

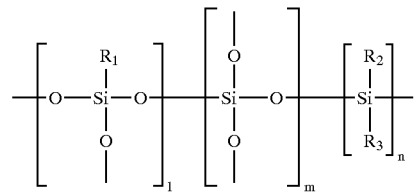

wherein each of R1, R2, and R3, which may be the same or different, is an aryl group, a hydrogen atom, an aliphatic alkyl group, a hydroxyl group, trialkylsilyl group, or a functional group having an unsaturated bond, and each to l, $m_2$ and n is an integer and $l+m+n \geq 1$, and the silicone polymer has a weight average molecular weight of not less than 1000.

General formula (2);

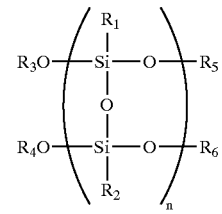

wherein each of R1 and R2, which may be the same or different, is an aryl group, a hydrogen atom, an aliphatic alkyl group, or a functional group having an unsaturated bond. Each of R3, R4, R5, and R6, which may be the same or different, is a hydrogen atom, an aryl group, an aliphatic alkyl group, a trialkylsilyl group, or a functional group having an unsaturated bond, n is an integer and at least 1, and the silicone polymer has a weight average molecular weight of not less than 1000.

Such a silicone polymer includes a polymer crosslinked and cured by light of ultraviolet ray or the like. As a preferable example thereof, there is pointed out a polymer in which 1% or more of substituent of R1, R2 and R3 is functional group having unsaturated bond in general formula (1), further, in general formula (2), there is pointed out a polymer in which 1% or more of substituent of R1, R2, R3, R4, R5 and R6 is functional group having unsaturated bond. Functional group having unsaturated bond is a reaction group for crosslinking polymer molecules by crosslinking reaction or radical reaction, although alkenyl group, alkylacryloyl group, alkylmethacryloyl group or styryl group is preferable, the reaction group is not limited thereto. The functional groups having unsaturated bond may be introduced by a single thereof or may be introduced as a mixture of two kinds or more thereof. Silicone polymer having such a photocrosslinking performance is advantageous in fabricating a sensor element in view of capable of progressing curing reaction at low temperature with light as driving force by itself or by combining with a photocrosslinking agent, a photoinitiator or a photosensitizer and capable of reducing temperature applied to the sensor element or capable of carrying out self-patterning without using resist.

The silicone resin film according to the invention can be formed by coating a solution of silicone polymer shown by the general formula (1) and/or general formula (2), so-to-speak varnish and heating and curing thereof. As a solution of such silicone polymer, a solvent solution of alcohol species, ketone species, ether species, halogen species, ester species, benzene species, alkoxybenzene species or cyclic ketone species, is suitable. The solution of silicone polymer may be added with silane coupling agent for promoting adherence with surface of the sensing portion, polymerizing monomer for promoting density of a cured film or initiator, crosslinking agent, photosensitizer or polymerization inhibitor for promoting preservation stability. Particularly, when there is used silicone polymer having photocrosslinking performance, there may be added photocrosslinking agent, photoinitiator or photosensitizer as mentioned above. Photocrosslinking agent or photoinitiator is an adding agent for causing to cure a film by radical reaction or crosslinking reaction and as a photocrosslinking agent, there is pointed out photosensitive compound forming radical active species by light irradiation such as aromatic azide compound, aromatic bisazide compound, iminoquinonediazide compound, aromatic diazo compound, or organic halogen compound, as photoinitiator, there is pointed out carbonyl compound, dicarbonyl compound, acetophenone, benzoin ether, acyl phosphine oxide, thioxanthone, aminocarbonyl compound or nitrogen including compound. Although temperature of curing processing differs by kind of polymer, heat resistant temperature of the sensing portion or heat resistant temperature of the sensor element per se before forming the protective film, normally, 100° C. through 400° C. is suitable, particularly, when there is used photocrosslinking polymer, mentioned above, curing processing can be carried out at comparatively low temperature of 100° C. through 250° C.

An explanation will be given of a sensor element according to the invention in reference to the attached drawings as follows.

FIG. 1($g$) is a sectional view for explaining an example of a magnetoresistance sensor according to the invention. A sensor main body 1 is a magnetoresistance sensor constituted by a substrate 1*a*, a substrate insulating film 1*b* formed above the substrate 1*a*, slender lines 1*c* constituting a sensing portion, a wiring 1*d* comprising a metal wire (Al, AlSi, Cu or the like) electrically connecting the slender lines 1*c* and a signal processing circuit (not illustrated) and a passivation film 1*f* comprising an inorganic film (silicon nitride film, silicon oxide film or the like) formed by a sputtering process or a CVD process and above the sensor main body 1, there is formed silicone resin film 2 to cover at least the sensing portion.

FIG. 1A through FIG. 1G are sectional views for explaining an example of a method of fabricating the magnetoresistance sensor according to the invention. First, above the sensor main body 1, there is coated varnish prepared by dissolving silicone polymer shown by the above-described general formula (1) and/or general formula (2) in a solvent of alcoholic species, ketone species, ether species, halogen species, ester species, benzene species, alkoxybenzene species, or cyclic ketone species by a film thickness of 10 nm through 50 $\mu$m, a heat treatment is carried out at 100° C. through 250° C. above a hot plate, and the silicone resin film 2 is formed above the sensor main body 1 (FIG. 1A).

Figure 1C:
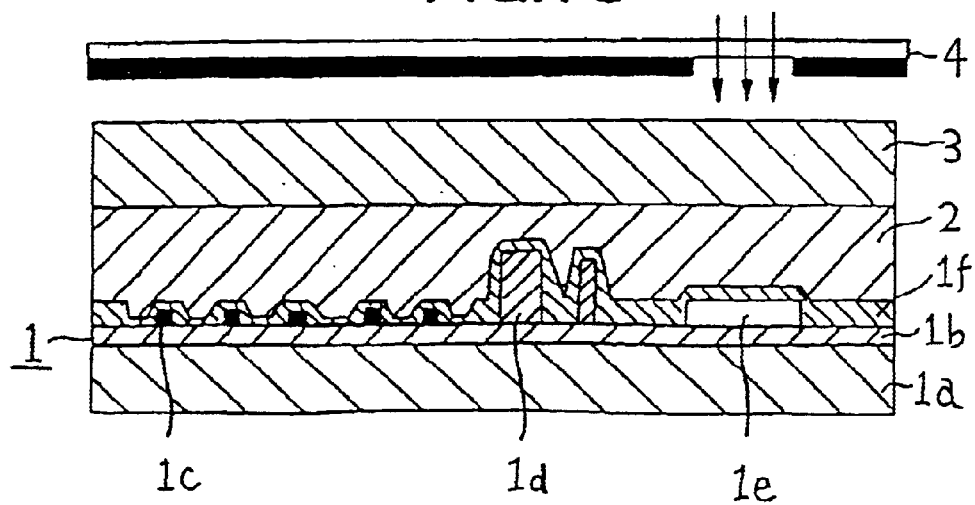

Next, there is applied an i-line positive resist 3 having a film thickness of 100 nm through 20 pm on the surface of the silicone resin film 2 (FIG. 1B), ultraviolet light (i-line) is irradiated through a mask 4 having a contact hole pattern for exposing the bonding pad 1*e* or dicing lines (not illustrated) of the sensor main body 1, and the i-line positive resist 3 of the contact hole portion is exposed (FIG. 1C).

Figure 1D:
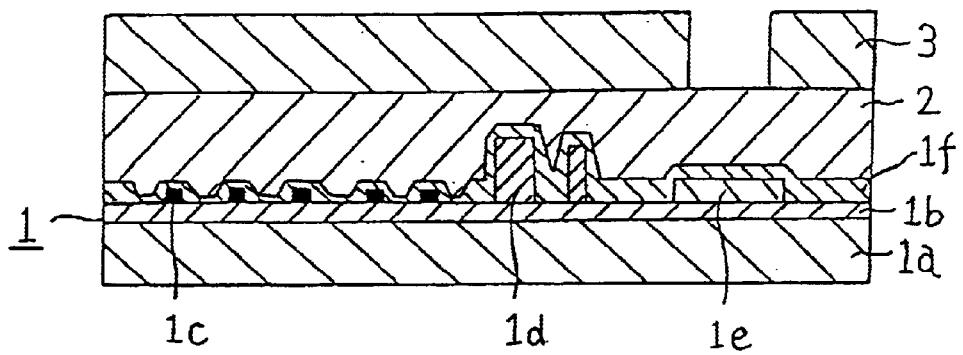

Next, developing processing is carried out after carrying out a baking operation after exposure to thereby provide a pattern of the i-line positive resist 3 having a desired pattern (FIG. 1D).

Figure 1E:
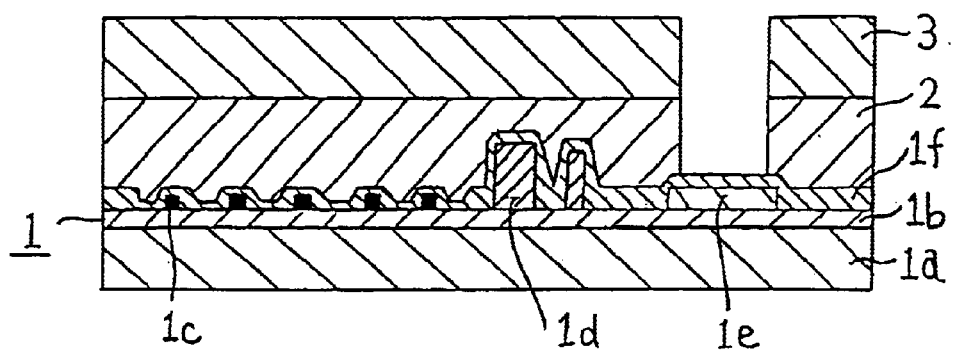
Figure 1F:
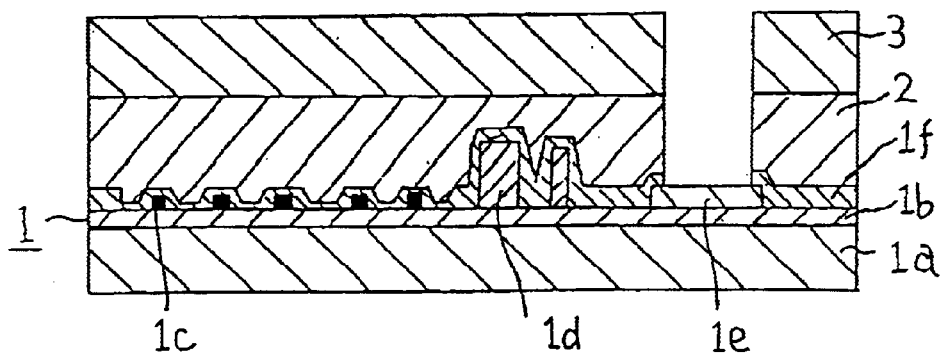

With the pattern of the i-line positive resist 3 as a mask, contact holes are provided by developing the silicone resin film 2. The developing processing is carried out by carrying out dipping development or spinning development by a developer exclusive for the silicone resin film and thereafter cleaning by a rinse solution exclusive for the silicone resin film (FIG. 1E).

Figure 1G:
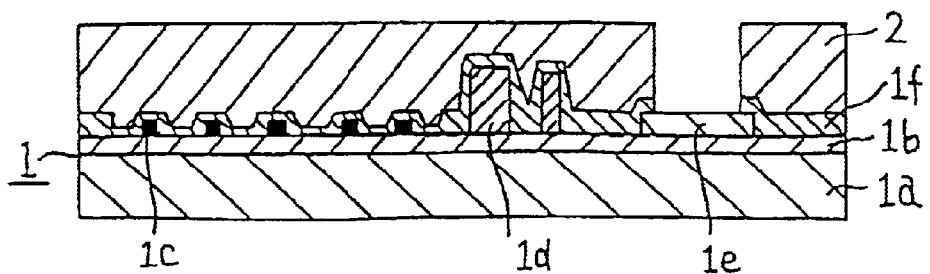

Next, after removing the passivation film 1*f* by a dry etching process (FIG. 1F), the i-line positive resist 3 above the silicone resin film 2 is removed in a wet state or removed in a dry state by using a reactive ion etching apparatus, an ion beam etching apparatus, oil an asking apparatus, and by using an oven or a hot plate, postbaking is carried out at 200° C. through 450° C. to thereby cure the silicone resin film 2. Thereby, there is provided the magnetoresistance sensor covered with the silicone resin film 2, a predetermined portion of which is opened (FIG. 1G).

According to the magnetoresistance sensor, a deterioration in the characteristic of the sensor can be prevented or a positional shift of the slender wire 1*c* or the wiring 1*d* can be prevented by covering the sensor with the silicone resin film 2. According to the silicone resin film 2, residual stress is low, buffer action is provided and therefore, stress from seal resin can be buffered and the positional shift or erroneous operation of the element thereby can be prevented. Further, when there is a control circuit for controlling the sensor main body, positional shift of wirings thereof can also be prevented. Further, the resin film is provided with heat resistance capable of resisting a fabrication process of the sensor element and is excellent in environment resistance and accordingly, the resin film is effective as the protective film of the sensor main body. Further, also in evaluation of characteristic of the sensor main body by a pressure cooker test, abnormality of characteristic is not recognized.

Further, according to the silicone resin film 2, the film is formed by rotational coating and accordingly, radiation damage of the sensor main body 1 by plasma irradiation can be avoided.

Further, it is preferable to include a large amount of hydroxyl group at a surface of the passivation film if in order to further promote the adhering performance with the silicone resin film 2.

Further, although the sensor main body 1 is an unlimitedly used for a sensor, particularly, a magnetoresistance sensor, an air flow sensor, an acceleration sensor, a pressure sensor, a yaw rate sensor or an image sensor is used as the sensor main body 1.

Further, the sensor main body 1 may include a control circuit for controlling the sensor main body 1.

Further, for the sensing portion (slender line) 1*c* of the sensor main body 1, although depending on a kind of the sensor, there is used a metal such as Au, Al, Ag, Bi, Ce, Cr, Cu, Co, C, Fe, Hf, In, Mo, Mg, Ni, Nb, Pb, Pt, Si, Sn, Ti, Ta, V, W, Zn, Zr or the like, alloy, oxide, nitride, silicide, sulphide, carbide, fluoride or the like comprising the metals. For example, there is used, as alloy, Al—Cu, Al—Si, Cu—Cr, Cu—Ni, Ni—Cr, Ni—Fe, Al—Si—Cu, Ni—Cr—Si, Al—Sc, Co—Cr or the like, as oxide, $Al_2O_3$, $CeO_2$, $CuO$, $Fe_2O_3$, $HfO_2$, $MgO$, $Nb_2O_5$, $SiO$, $SiO_2$, $TiO$, $TiO_2$, $Ta_2O_5$, $ZrO_2$ or the like, as nitride, $AlN$, $Cr_2N$, $Si_3N_4$, $TiN$, $ZrN$ or the like, as silicide, $CrSi_2$, $MoSi_{2.5}$, $WSi_2$, $Wsi_{0.4}$ or the like, as sulphide, $ZnS$, as carbide, $SiC$, $TiC$, $WC$ or the like and as fluoride, $MgF_2$ or the like, however, these are not limited to the above-described and any material may be used so far as the material is a material necessary for fabricating the sensor.

Further, the adhering performance between the sensor main body 1 and the silicone resin film 2 may be intensified by processing the surface of the sensor main body 1 by a solution or the like including a silane coupling agent before coating the varnish.

Further, adhering performance between the i-line positive resist 3 and the silicone resin film 2 may be intensified by processing the surface of the silicone resin film 2 by hexamethylenedisilazane or the like after coating the varnish. Further, a reflection preventive film may be formed to form the pattern shape accurately.

Further, although according to the above-described explanation, the i-line positive resist 3 is used, so far as a desired pattern can be formed, either of positive resist and negative resist may be used and any of resist for g-line, for i-line, for KrF excimer and for ArF excimer may be used.

Further, before developing the silicone resin film 2, ultraviolet ray may be irradiated to an entire face of a pattern of the i-line positive resist 3 to thereby increase crosslinking density to thereby promote resistance against a developer or a rinse solution,exclusive for the silicone resin film Further, the silicone resin film 2 may be removed by the dry etching process in place of the processing of developing the silicone resin film 2. That is, the silicone resin film 2 is cured after forming thereof to thereby constitute a cured film, thereafter, the pattern of the i-line positive resist 3 is formed by normal photolithography at an upper layer thereof and with the pattern of the i-line positive resist 3 as a mask, the silicone resin film 2 and the passivation film 1f are continuously etched in a dry state by using a reactive ion etching apparatus or an ion beam etching apparatus.

Although an etching gas used in reactive ion etching is not particularly limited so far as the gas is gas species capable of etching the silicone resin film 2, a mixed gas of fluorine species gas such as $CF_4$, $CHF_3$ or $C_4F_8$ and Ar or $O_2$ can preferably be used.

Further, when the pattern is formed by reactive ion etching using an etching gas including oxygen or when the i-line positive resist 3 is removed by using an asking apparatus, oxidation of a surface layer of the silicone resin film 2 can be reduced when the operation is carried out under a low pressure condition and a lower power condition. Particularly, oxidation of the surface of the silicone resin film 2 can further be reduced by a low pressure condition equal to or lower than 1 Torr and a low power condition equal to or lower than 1 kW.

When the silicone resin film 2 is removed by the dry etching process in this way, the silicone resin film 2 and the passivation film if can continuously be removed and accordingly, the process can be simplified.

Further, the magnetoresistance sensor may be provided with seal resin. After covering the sensor main body 1 with the silicone resin film, the bonding pad 1e and a lead frame (not illustrated) are connected by a bonding wire (not illustrated) and a total of the substrate is sealed by mold resin such as epoxy resin. In this case, a control circuit for controlling the sensor main body 1 may be included on the same substrate.

Further, although according to the above-described example, the silicone resin film 2 is laminated above the sensor main body 1 protected by the passivation film 1f such as a silicon nitride film or a silicon oxide film formed by a sputtering process or a CVD process to function particularly as a stress buffer coating film, the silicone polymer described in general formula (1) or general formula (2) is highly pure and therefore, the silicone resin film 2 may directly be laminated on the sensor main body which is not protected by the passivation film to thereby serve both as a protective film and a stress buffer coating film.

Further, it is preferable that the passivation film 1f includes a large amount of hydroxide group at its surface to further promote the adhering performance with the silicone resin film 2.

Figure 2A:
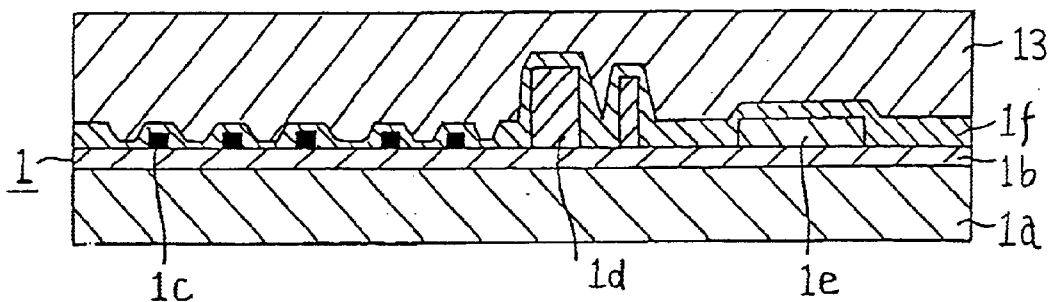
FIGS. 2A–2D are sectional views for explaining another example of a structure of a magnetoresistance sensor according to the invention and a method of fabricating thereof.
Figure 2B:
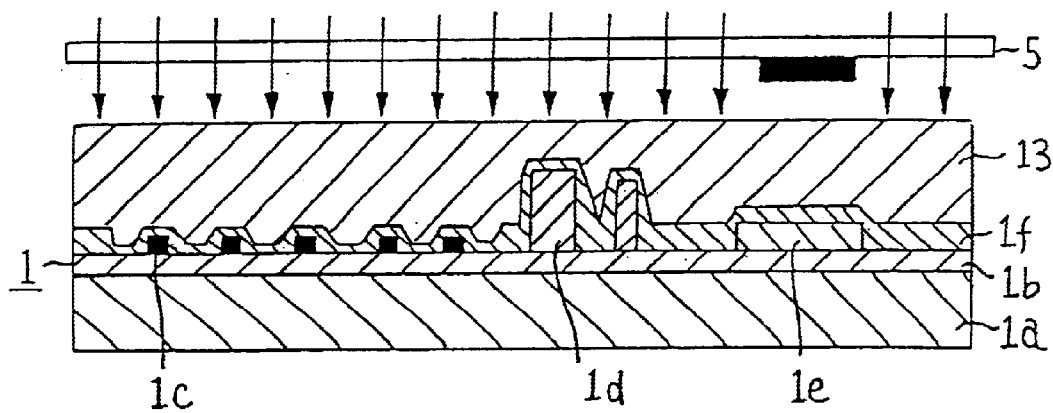
Figure 2C:
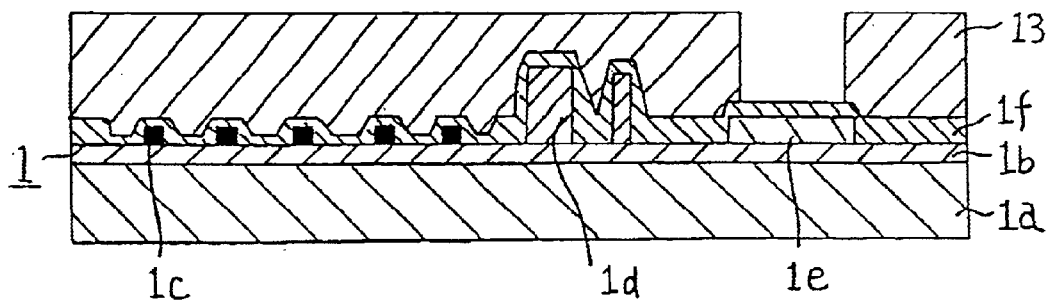
Figure 2D:
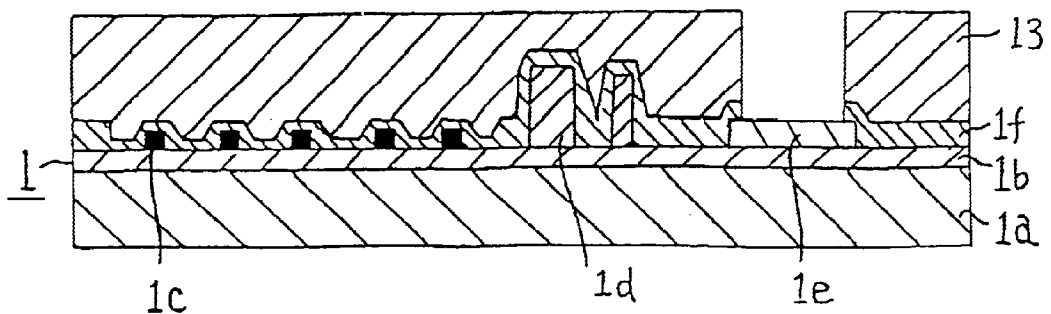

FIG. 2D is a sectional view explaining another example of a magnetoresistarice sensor according to the intention. Although the constitution of the sensor main body 1 is the same as that of FIG. 1G, above the sensor main body 1, there is formed a silicone resin film 13 which is photocured to cover at least the sensing portion.

FIGS. 2A through 2D are sectional views for explaining another example of a method of fabricating a magnetoresistance sensor according to the invention. The method of fabricating the magnetoresistance sensor differs from the above-described method in that there is used a compound prepared by dissolving a polymer having a photocrosslinking characteristic in a solvent and adding a photocrosslinking agent or a photopolymerization agent thereto. The silicone resin film is cured by irradiating and exposing through a mask 5 having a desired pattern, removing the silicone resin film at a portion which is not irradiated with light by developing, and postbaking at 100° C. through 250° C. (FIGS. 2B and C). When the passivation film 1f is removed by the dry etching process, there is provided the magnetoresistance sensor covered with the silicone resin film 13 which is cured optically and a predetermined portion of which is opened (FIG. 2D).

The photocrosslinking agent or the photoinitiator is normally added for causing reaction with light as driving force and is decomposed also by a heat treatment to thereby cause curing reaction. The polymer is formed on the sensor element and therefore, a temperature condition of curing thereof directly effects adverse influence on the characteristic of the sensor, however, the polymer having high molecular weight is provided with heat resistance at 500° C. even when the polymer is not thermally cured, by adding the additives, curing temperature in forming the film can be lowered and the polymer can be cured at temperature equal to or lower than heat resistance limit temperature of the sensor element. Further, by adding the additives, photosensitivity is manifested, when a pattern needs to transcribe on the resin film, by irradiating ultraviolet ray directly to the resin film via a mask having a desired pattern and developing thereof, the pattern can be formed, the resist pattern forming step can be dispensed with, the pattern can be transcribed in a short period of time and stably and accordingly, the additives can contribute to simplification and low cost formation of the process.

Embodiment 1

Figure 3A:
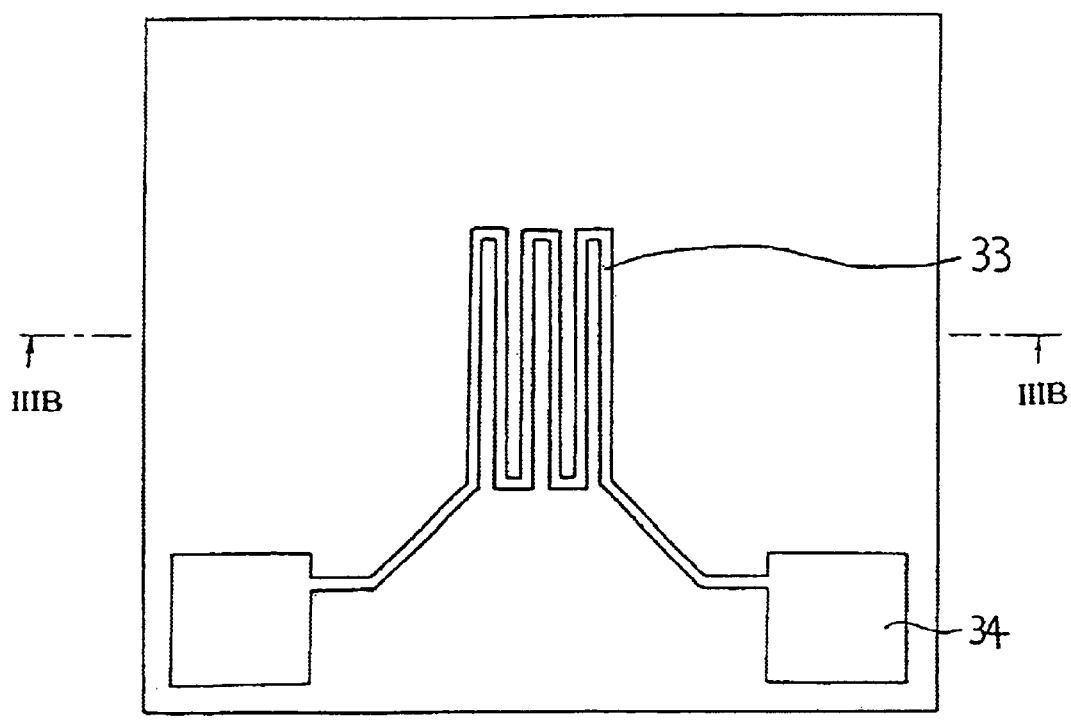
Figure 3B:
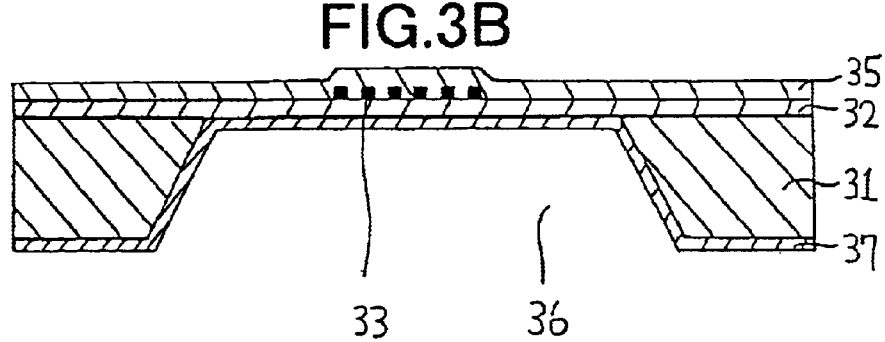

FIGS. 3A and 3B illustrate views for explaining a structure of an air flow sensor of Embodiment 1 according to the invention in which FIG. 3A is a plan view and FIG. 3B is a sectional view taken along a line IIIB—IIIB of FIG. 3A.

An air flow sensor according to the invention is formed with a metal wire 33 in a zigzag shape constituting a sensing portion above a lower support film 32 formed above a silicon substrate 31 and bonding pads 34 provided to connect to both ends of the metal wire 33 for detecting a change in an electric resistance value, an upper support film 35 is formed above surfaces of these, further, the silicon substrate 31 is provided with a recess portion 36 for exposing the sensing portion and at least a surface on the rear face side of the sensing portion is covered with a silicone resin film 37.

The air flow sensor detects a flow rate of a gas by detecting a heat amount of the metal line 33 which is conducted and heated and which is deprived by depending upon the flow rate of the gas passing through the recess portion 36 by a change in the electric resistance value.

An explanation will be given of a method of fabricating the air flow sensor. First, after forming the lower support film 32 comprising a silicon nitride film formed by a sputtering apparatus above the Si substrate 31 having a thickness of about 300 $\mu$m, the metal line 33 comprising Pt constituting the temperature sensor, the bonding pads 34 and the upper support film 35 comprising a silicon nitride film were formed in this order, a portion of the Si substrate 31 right under the metal line 33 comprising Pt was removed by a wet etching process. At this occasion, there is formed a stepped difference of 300 μm at the rear face of the sensing portion.

Next, the pattern of the silicone resin film 37 was formed on the surface on the rear face side of the sensing portion by the following method.

First, an aqueous solution including N-phenyl-γ-aminopropyltrimethoxysilane was rotationally coated on the rear face of a silicon wafer by using a spinner at 2000 rpm, dried above a hot plate for 1 minute at 120° C. to thereby carry out a surface treatment. The surface treatment is carried out to promote adhering performance with the lower support film 32.

Silicone polymer of general formula (1) in which 30 mol % of side chains R1, R2 and R3 is vinyl group, remaining side chains are methyl group, l/m/n ratio is 5/3/2 and weight average molecular weight is 10000 was dissolved in methoxybenzene to constitute 25 wt % and the polymer was added with 10 weight % of 1-hydroxy-cyclohexylphenylketone, 3 weight % of 3-ketocoumalin and 1 weight % of triethanolamine. The varnish was rotationally coated to the surface on the rear side of the lower support film 32 comprising a silicon nitride film subjected to the surface treatment at 3000 rpm and was subjected to a heat treatment above a hot plate for 2 minutes at 130° C. to thereby remove the solvent. Further, postbaking was carried out in an oven under flow of nitrogen for 1 hour at 400° C. to thereby completely cure the varnish to thereby form the silicone resin film 37 having a film thickness of about 1 μm.

The i-line positive resist was rotationally coated on the silicone resin film 37 to constitute a film thickness of about 3 μm and normal photolithography was carried out to thereby provide i-line positive resist pattern for opening desired dicing lines.

Next, with the i-line positive photoresist pattern as a mask, a portion of the silicone resin film which is not protected by the i-line positive resist, was removed by a dry etching process. The dry etching was carried out by using a reactive ion etching apparatus and using a gas having a mixture ratio of $CF_4/O_2$ of 7/3 as the gas for the dry etching. Further, the i-line positive resist was ashed to remove by oxygen plasma to thereby provide an air flow sensor covered with the silicone resin film 37 a predetermined portion of which was opened.

After forming the silicone resin film 37, the bonding pads 34 and a lead frame (not illustrated) were connected by bonding wires (not illustrated).

According to the air flow sensor, the metal line 33 comprising Pt which is conducted with electricity, is heated to temperature higher than outside temperature by about 100° C. and the metal line 33 comprising Pt is deprived of heat and temperature thereof is lowered by depending upon flow intensity of gas flow. The resistance value of the metal line 33 comprising Pt is changed by temperature thereof and therefore, the deprived heat amount can electrically be detected. The deprived heat amount and the flow intensity of the gas flow correspond to each other in a one-to-one relationship and accordingly, the flow of gas can be known. In the case of a sensor not covered with the silicone resin film, there poses a problem that the sensor is gradually deteriorated by impurity or steam from outside air, there is a difference in the characteristic of the sensor individually, however, by coating the sensor with the silicone resin film 37, the sensor is protected from outside air, the characteristic of the sensor was not deteriorated and a result of a durability test thereof was at a practical level. Further, excellent characteristic of the sensor was achieved and a dispersion in the characteristic of the individual sensor was also resolved.

Embodiment 2

FIG. 1G is a sectional view for explaining a structure of a magnetoresistance sensor of Embodiment 2 according to the invention. The passivation film 1f of the sensor main body 1 is a silicon nitride film having a film thickness of about 800 nm formed by a sputtering apparatus and the silicone resin film 2 was formed on the surface of the passivation film 1f by the following method.

First, silicone polymer of the general formula (2) in which 15 mol % of side chains R1 and R2 are allyl group, remaining side chains are phenyl group, side chains R3, R4, R5 and R6 are hydrogen atom and weight average molecular weight is 200000 was dissolved to mothoxybenzene to constitute 20 wt %, further, the polymer was added with 5 wt % of 2,6-bis (4'-azidebenzal) methylcyclohexanone and 0.5 weight % of γ-aminopropyltrimethoxysilane. The varnish was rotationally coated to an upper portion of the passivation film by speed of 2500 rpm, and subjected to a heat treatment above a hot plate for 2 minutes at 130° C. to thereby remove solvent. There was carried out tight contact exposure via a photomask having patterns of desired bonding pads and dicing lines and unexposed portions were dissolved and removed by a developer of methoxybenzene/isopropyl alcohol=1/4 (volume ratio) to thereby finish patterning of the silicone resin film. Further, postbaking was carried out in an oven under flow of nitrogen for 1 hour at 250° C. to thereby completely cure the film and the silicone resin film 2 of a film thickness of about 5 μm having a desired pattern was formed.

After forming the silicone resin film 2, the bonding pads 34 and a lead frame (not illustrated) were connected by bonding wires (not illustrated) and a total of the substrate was sealed by epoxy resin. By covering the sensor main body by the silicone resin film, there were resolved positional shift of the wiring 1d comprising AlSi and the slender line 1c comprising a magnetic metal indicating the magnetoresistance effect, crack of the nitride film and deterioration of the sensor characteristic accompanied thereby, which had originally been caused by stress in forming seal resin.

Embodiment 3

Figure 4A:
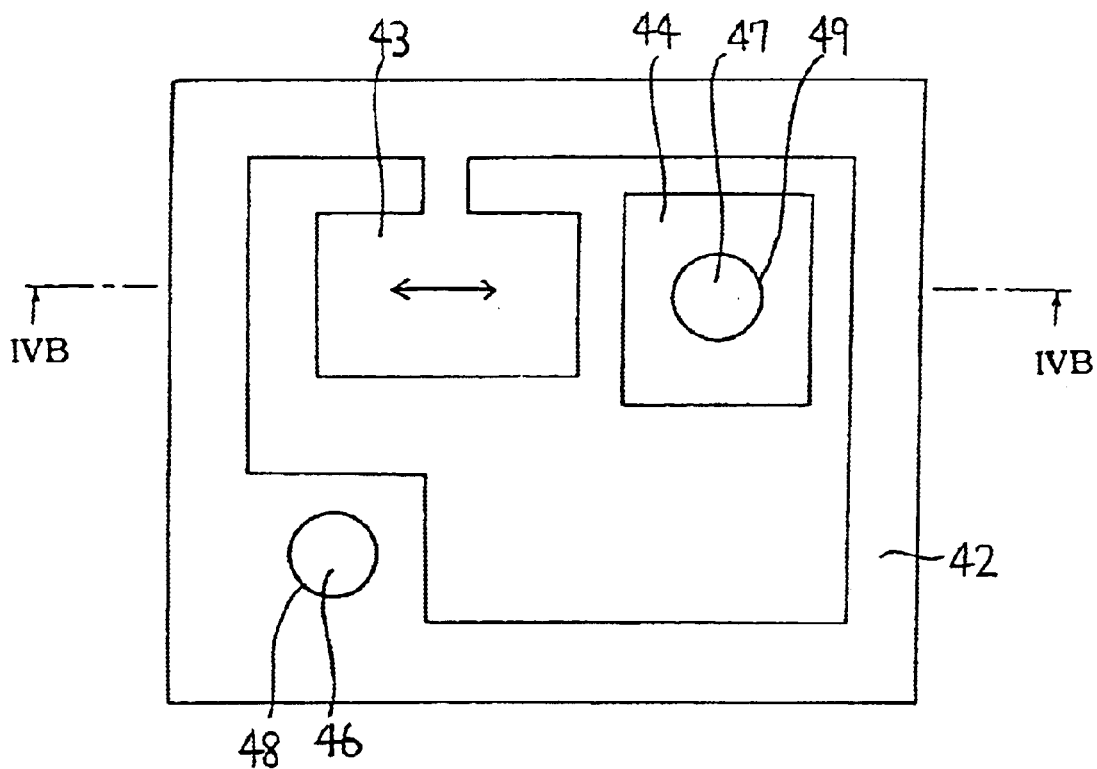
Figure 4B:
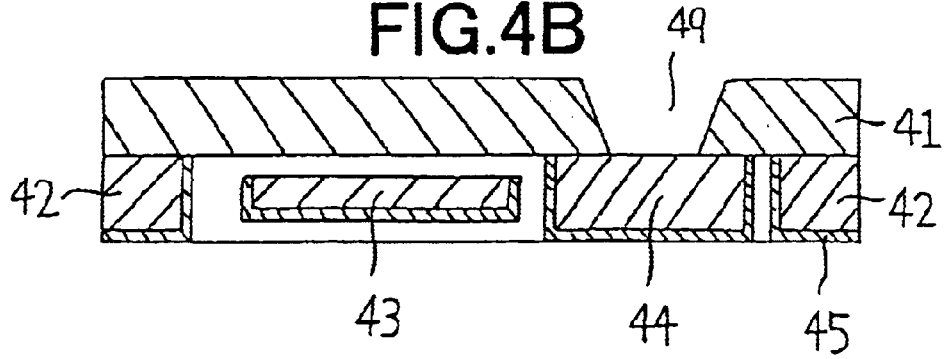

FIGS. 4A and 4B are views for explaining a structure of an acceleration sensor of Embodiment 3 according to the invention in which FIG. 4A is a plan view and FIG. 4B is a sectional view taken along a line IVB—IVB of FIG. 4A.

An acceleration sensor according to the invention includes a silicon substrate 42 in the shape of a frame along a periphery of a glass substrate 41, a sensing portion 43 projecting from the silicon substrate 42 above a plane at a constants distance from the glass substrate 41, and an opposed electrode 44, contiguous to the sensing portion 43, forming an electric capacitance between opposed side faces of the opposed electrode 44 and the sensing portion 43. Further, a surface and side faces of the sensing portion 43 are covered with a silicone resin film 45. Bonding pads 46 and 47 are used for detecting the electric capacitance between the silicon substrate 42 having the frame shape and the opposed electrode 44. Further, contact holes 48 and 49 are located at portions of the glass substrate opposite the bonding pads 46 and 47.

The acceleration sensor detects acceleration by a change in the electric capacity accompanied by a change in a distance between the side face of the sensing portion 43 and the side face of the opposed electrode 44 by displacing the sensing portion 43 in accordance with acceleration.

An explanation will be given of a method of fabricating the acceleration sensor. First, both faces of a portion of the silicon substrate having a thickness of 300 through 500 μm for constituting the sensing portion, was etched to a predetermined depth by a wet etching process and the glass substrate 41 was pasted by anodic bonding to an upper face of a portion of the silicon substrate which was not etched. Thereafter, portions of the silicon substrate other than portions constituting the silicon substrate in the frame shape, the sensing portion and the opposed electrode, were removed to penetrate the silicon substrate to the glass substrate by wet etching to thereby form the silicon substrate 42 in the frame shape, the sensing portion 43 and the opposed electrode 44. At this occasion, there is formed a stepped difference of 300 through 500 μm at side faces of the silicon substrate 42 in the frame shape and the opposed electrode 44. The silicone resin film 45 was formed at the rear face and the side face of the acceleration sensor main body formed in this way by the following method.

First, silicone polymer of general formula (2) in which all of side chains R1 and R2 are phenyl group, side chains R3, R4, R5 and R6 are trimethylsilyl group and weight average molecular weight is 150000, was dissolved to methoxybenzene by 20 weight % relative to the solution and γ-aminopropyltrimethoxysilane was dissolved thereto by 0.5 weight % relative to the polymer to thereby prepare varnish.

The varnish was rotationally coated onto the rear face of the acceleration sensor main body at speed of 2000 rpm, subjected to a heat treatment above a hot plate for 5 minutes at 150° C. to thereby remove the solvent to thereby form the silicone resin film 45 having a film thickness of about 6 μm. The i-line positive resist was rotationally coated onto the silicone resin film 45 to constitute a film thickness of about 6 μm and normal photolithography was carried out. That is, after prebaking, the film was exposed via a photomask having a desired pattern and after exposure, baking, developing and postbaking were carried out to thereby form a desired positive resist pattern for i-line.

Next, with the pattern of the positive resist for i-line as a mask, by a developer of methoxybenzene/xylene=1/4 (volume ratio), portions of the silicone resin which are not protected by the i-line positive resist, was dissolved and removed, the i-line positive resist was removed by a solvent strip such as butyl acetate, thereafter, postbaking was carried out at 300° C. through 450° C. in an oven under nitrogen atmosphere to thereby completely cure thereof to thereby provide the silicone resin film 45 a predetermined portion of which was opened.

The contact holes 48 and 49 were formed at portions of the glass substrate 41 above the silicon substrate 42 in the frame shape and the opposed electrode 44 and the bonding pads 46 and 47 respectively in correspondence with the sensing portion and the opposed electrode were exposed. The bonding pads 46 and 47 and a lead frame (not illustrated) were connected by bonding wires (not illustrated).

When operation of the acceleration sensor covered with the silicone resin film 45 was confirmed, in accordance with acceleration, the sensing portion 43 was displaced in a direction in which the distance between the sensing portion 43 and the opposed electrode 44 is changed (arrow direction of FIG. 4A). The change in the interval between the side face of the sensing portion 43 and the side face of the opposed electrode 44 was detected as a change in the capacitance and it was verified that there was provided a sensitivity of a sufficiently practical level.

Industrial Applicability

As mentioned above, the sensor element according to the invention is suitable for achieving promotion of reliability of the sensor main body and is suitable for being used in, for example, a magnetoresistance sensor, an air flow sensor, an acceleration sensor, a pressure sensor, a yaw rate sensor and an image sensor.

What is claimed is:

1. A magnetoresistance sensor element comprising:
   a sensor substrate; and
   a sensing portion comprising slender wires supported by the sensor substrate, wherein
      the surface of the sensing portion is covered with a film of a cured silicon polymer,
      the silicone polymer of the cured silicon polymer film is represented by the following general formula

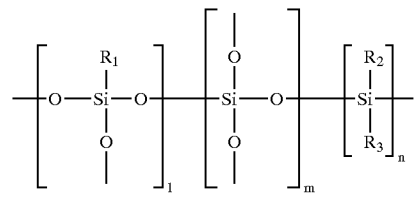

R1, R2, and R3, which may be the same or different, are selected from the group consisting of an aryl, hydrogen, an aliphatic alkyl, a hydroxyl, a trialkylsilyl, and a functional group having an unsaturated bond,
   l, m, and n are integers and l+m+n≧1, and the silicone polymer has a weight average molecular weight of not less than 1000.

2. A magnetoresistance sensor element comprising:
   a sensor substrate; and
   a sensing portion comprising slender wires supported by the sensor substrate, wherein
      the surface of the sensing portion is covered with a film of a cured silicon polymer,
      the silicone polymer of the cured silicon polymer film is represented by the following general formula

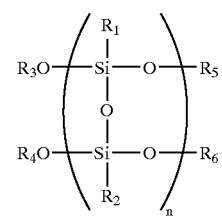

R1 and R2, which may be the sane or different, are selected from the group consisting of an aryl, hydrogen, an aliphatic alkyl, and a functional group having an unsaturated bond,
   R3, R4, R5, and R6, which may be the same or different, are selected from the group consisting of hydrogen, an aryl, an aliphatic alkyl, a trialkylsilyl, and a functional group having an unsaturated bond,
   n is an integer and at least 1, and
   the silicone polymer has a weight average molecular weight of not less than 1000.

3. The magnetoresistance sensor element according to claim 1 wherein the silicon polymer is a photocured polymer.

4. The magnetoresistance sensor element according to claim 2 wherein the silicone polymer is a photocured polymer.

5. A method of fabricating a magnetoresistance sensor comprising:

coating a sensing portion comprising slender wires supported by a sensor substrate with a solution of a silicone polymer; and heating and curing the solution to form a silicone resin film on the sensing portion.

6. The method of fabricating a magnetoresistance sensor element according to claim 5, wherein the silicone polymer is represented by the following gene+ral formula

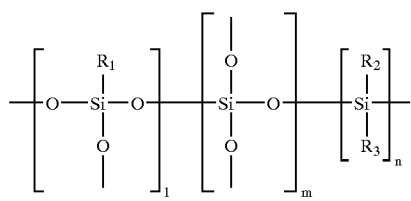

wherein

R1, R2, and R3, which may be the same or different, are selected from the group consisting of an aryl, hydrogen, an aliphatic alkyl, a hydroxyl, a trialkylsilyl, and a functional group having an unsaturated bond.

l, m, and n are integers and l+m+n is $\geq 1$, and the silicone polymer has a weight average molecular weight of not less than 1000.

7. The method of fabricating a magnetoresistance sensor element according to claim 5, wherein the silicone polymer is represented by the following general formula

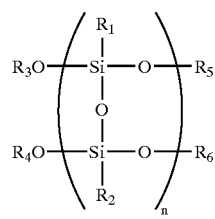

wherein

R1 and R2, which may be the same or different, are selected from the group consisting of an aryl, hydrogen, an aliphatic alkyl, and a functional group having an unsaturated bond, R3, R4, R5, and R6, which may be the same or different, are selected from the group consisting of hydrogen, an aryl, an aliphatic alkyl, a trialkylsilyl, and a functional group having an unsaturated bond, n is an integer and at least 1, and the silicone polymer has a weight average molecular weight of not less than 1000.

8. The method of fabricating a magnetoresistance sensor element according to claim 6 including curing the silicone polymer with light.

9. The method of fabricating a magentoresistance sensor element according to claim 7 including curing the silicone polymer with light.

10. The method of fabricating a magnetoresistance sensor element according to claim 5 including curing the solution at a temperature from 100° C. to 250° C.

* * * * *